United States Patent [19]
Teng et al.

[11] Patent Number: 5,137,912
[45] Date of Patent: Aug. 11, 1992

[54] CHELERYTHRINE INHIBITS PLATELET AGGREGATION—A POTENTIAL ANTI-AGGREGATION DRUG

[75] Inventors: Che-Ming Teng; Ih-Sheng Chen; Tur-Fu Huang; Feng-Nien Ko; Shwu-Jen Wu, all of Taipei, Taiwan; Shwu-Jen Wu, both of Taipei, Taiwan

[73] Assignee: National Science Council of Republic of China, Taipei, Taiwan

[21] Appl. No.: 646,373

[22] Filed: Jan. 28, 1991

[51] Int. Cl.$^5$ .................... A61K 31/335; A61K 31/34
[52] U.S. Cl. .................... 514/463; 514/468; 514/822
[58] Field of Search ............... 424/195.1; 514/182, 514/468, 463, 822

[56] References Cited

U.S. PATENT DOCUMENTS

4,590,061 5/1986 Southard .................... 424/7.1
4,767,626 8/1988 Cheng .................... 424/195.1

OTHER PUBLICATIONS

Chem. Abstr. 113(9):71037e, 1990.
The March Index 9th ed. p. 257, No. 2007, 1976.

*Primary Examiner*—John W. Rollins
*Attorney, Agent, or Firm*—Fleit, Jacobson, Cohn, Price, Holman & Stern

[57] ABSTRACT

This invention refer to chelerythrine, a considerably effective drug in the prevention and therapy of the thrombosis, which is a quaternary amine derivative and a major component of the organic solvent soluble extract of *Zanthoxylum simulans*. The effects of chelerythrine on the thromboembolism and the constriction of the blood vessel are also examined.

2 Claims, 4 Drawing Sheets

CHELERYTHRINE INHIBITS PLATELET AGGREGATION—A POTENTIAL ANTI-AGGREGATION DRUG

BACKGROUND OF THE INVENTION

Thrombosis, or sometimes refered as thromboembolism, is the clot of blood in a blood vessel or a cavity of the heart. It is usually formed by the interaction of the damaged blood vessel wall with the blood components such as platelet or other clotting factors. The damaged blood vessel wall is usually caused by elevated level of plasma cholesterol or triglyceride or other factors that damaged the lining endothelium. When a blood vessel is damaged, the endothelium is disrupted and an underlying layer of collagen is exposed. The exposed collagen attracts platelets, which adhere to it and liberate clotting factors. The clotting factors in turn rapidly attracts more platelets, and a loose plug of aggregated platelets is formed. The loose aggregation of platelets in the temporary plug is bound together and converted into the definitive clot by fibrin. These clots eventually caused the myocardial infarction and cerebral thrombosis, which are common symptoms among the adults population in the recent years. In spite of intensive researches for an effective anti-platelet aggregation drug, there is no drug to date that can effectively prevent the thrombosis except for the aspirin and dipyridamole, which are known as platelet aggregation inhibitors and used to inhibit the formation of blood clot. Breakthrough has yet to be achieved.

In addition, blood vessel abnormality and blood vessel constriction can also contribute to the formation of thrombosis. The cause to the abnormality of blood vessel is described previously. The blood vessel constriction, also known as blood vessel dilation is seen when blood factors such as prostacyclin (PG12) or endothelium-derived relaxing factor (EDRF) are released, that can relax the blood vessel and increase the blood flow. There is no drug to date that can prevent damages to the endothelium or stimulate the release of the PG12 or EDRF; although several calcium channel blockers such as nifedipine or verapamil can inhibit the calcium influx and cause the blood vessels to relax. The inventor has carefully examined the potential drug for the prevention of thrombosis and found that chelerythrine, the major components of *Zanthoxylum simulans*, have the activity against the thrombosis. This finding stimulated the inventor to investigate further and complete the present invention.

BRIEF DESCRIPTION OF THE DRAWINGS

The present invention will be described in reference to the annexed drawings which are given by way of example only, in which.

DESCRIPTION OF THE DISCLOSURE

Figure 1:
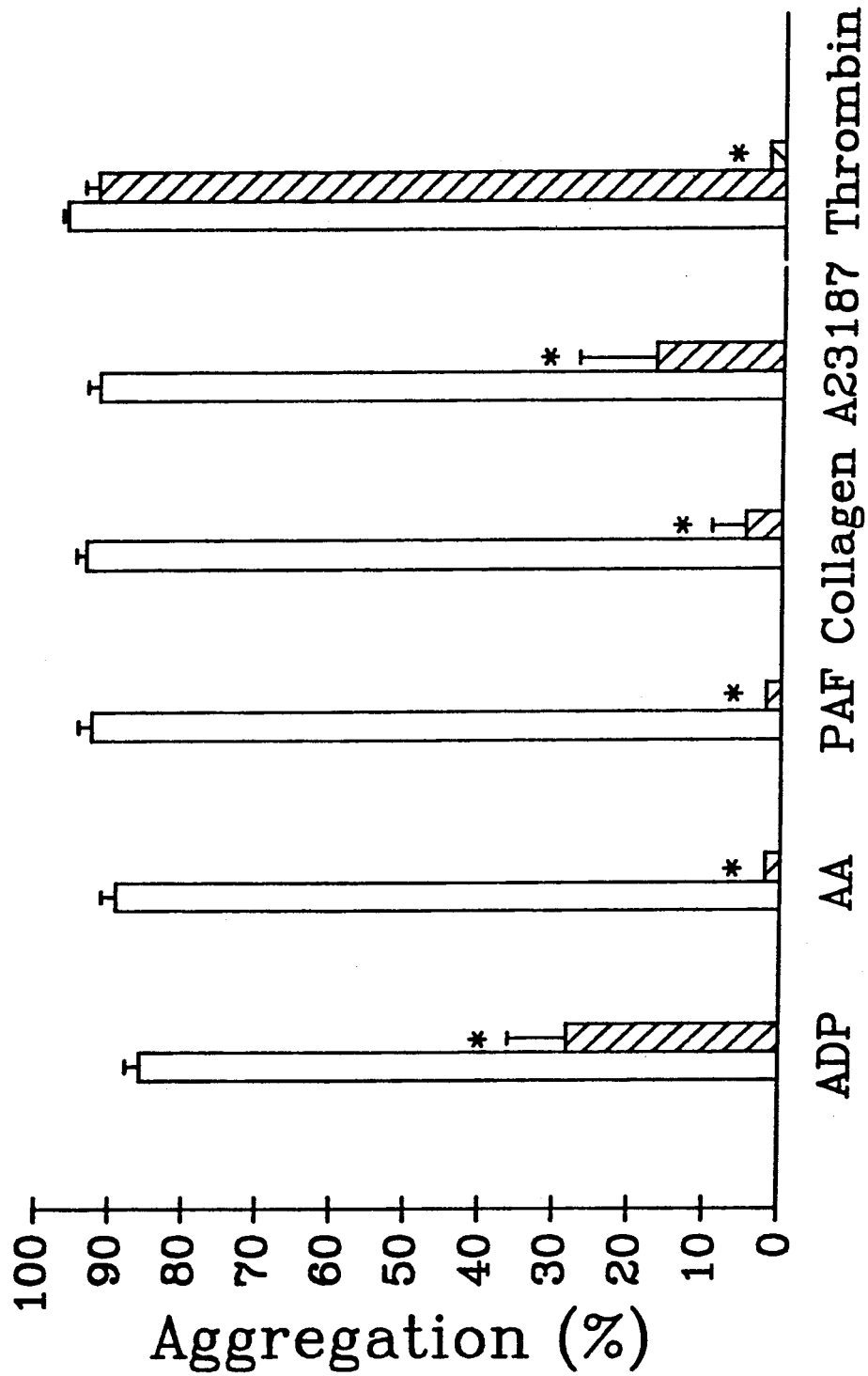
FIG. 1 shows the effect of chelerythrine on the platelet aggregation induced by some aggregation inducers. Washed rabbit platelets were preincubated with chelerythrine (10 μg/ml,▨; 20 μg/m,▨) or DMSO (0.5%,☐) at 37° C. for 3 min, then the inducer ADP (20 μM), arachidonic acid (AA, 100 μM), PAF (2 ng/ml), collagen (10 μg/ml), ionophore A23187 (5 μm) or thrombin (0.1 U/ml) was added. Values are presented as means±S.E. (n=5-7). *: $P<0.001$ as compared with the respective control.

Chelerythrine can be extracted from the root bark of *Zanthoxylum simulans* by the procedure described below: The pulverized dry root bark of the *Zanthoxylum simulans* was refluxed with methanol and then concentrated under reduced pressure. The residue was acidified with 5% acetic acid for extraction of the base. The acidic solution was made alkaline with $NH_4OH$ solution, and extracted with chloroform. The chloroform solution was shaken with 5% NaOH solution, then dried with anhydrous $K_2CO_3$ and concentrated. Then, 10% HCl was added to yield yellowish precipitate. This yellowish precipitate was recrystallized repeatedly with ethyl ether/methanol to obtain chelerythrine.

Examining the biological activities of the chelerythrine to the rabbit platelet, it was found that chelerythrine of the *Zanthoxylum simulans* has a strongly inhibitory effect on the platelet aggregation induced by the strong aggregation inducer such as arachidonic acid, or collagen. Therefore, it is predictive that chelerythrine can prevent the formation of thrombus. In the experiments that determined the effect of chelerythrine on the calcium-dependent constriction of rat aorta induced by high $K^+$ depolarization, the rabbit aorta was incubated in a solution containing high concentration of $K^+$, and then calcium was added to induce the constriction. The constriction is increased with the increase of calcium concentration. With the aorta pretreated with chelerythrine, the constriction is no longer observed even in the presence of calcium solution. When the aorta was preincubated with the same solution, in the presence of 3 uM of norepinephrine, the aorta will exhibit a phasic or tonic constriction. These phenomena can nevertheless be inhibited by the addition of chelerythrine. Substitution of $Ca^{++}$ with EDTA, the chelerythrine also showed the same inhibitory effects. Here, the effect of chelerythrine is believed to prevent the calcium influx into the cells, it obviously can influence the flow of cellular calcium ions as well. Even in the experiment where the rabbit aorta was pretreated with 3 uM of norepinephrine, and the chelerythrine was added later, the phasic or tonic constriction was still not observed.

In clinical trials, the formulated chelerythrine combined with a pharmaceutically acceptable substances, such as inert diluents, inert carrier, lubricant or buffering agents, to form a pharmaceutical composition usually in the forms of capsules, pills, tablets, powders, or injection, may be administered to the patients safely according to the need. The exact dose and regimen for administration of these compounds and compositions varies considerably, will necessarily be dependent upon the needs of the individual subject being treated, and the judgement of the medical practioner based on the patients' symptoms, weight, and age. Dosages between 10 to 200 mg for adults were usually preferred. The chelerythrine in this invention is shown effective, in the areas of thrombosis prevention, anti-inflammation, inhibition of the platelet aggregation, and vascular dilation.

PREPARATION OF PLATELET FROM RABBIT

Blood sample removed from the veins of the rabbit ear was adjusted with sodium citrate (3.8%, 1:9 v/v). Centrifugation at room temperature at 90×g for 10 min gave two separated layers. The upper layer, the platelet-rich plasma (PRP) was usually adjusted with platelet-poor plasma (PPP) to a density of $4.5 \times 10^8$ platelets/ml (cell counter ZM model) as the stock. On the other hand, the lower layer was further centrifuged at 500×g for 10 min and the upper layer thus obtained was used as PPP.

PLATELET AGGREGATION ASSAY

The assay followed the method of O'Brien (J. Clin. Path. 15, 452–456, 1962). In general, platelet aggregation was induced by the addition of aggregate enhancer such as adenosine diphosphate (ADP), collagen, arachidonic acid, thrombin, ionophore A23187 or PAF. The degree of aggregation was estimated from the change of the UV absorbance of PRP using the following formula:

degree of aggregation $(\%) = (A0 - Ai)/(A0 - At)$

Wherein
A0: UV absorbance of PRP before aggregation
Ai: UV absorbance of PRP after aggregation induced by an enhancer.
At: UV absorbance of PPP in the presence of Tyrode's solution.

The change of the UV absorbance in response to the addition of Tyrode's solution is usually taken as 100% aggregation.

The inhibitory effect of the compounds claimed in the present invention on the platelet aggregation is usually defined as follow:

degree of inhibition $(\%) = (1 - C_o/C_1) \times 100\%$,
wherein $C_o$: maximal degree of aggregation in the presence of compounds claimed in the present invention.
$C_1$: maximal degree of aggregation in the presence of 0.5% of DMSO.

The following examples are given to further illustrate the biological activities of the claimed compounds. These are not intended as limiting since numerous modifications and variations therein will be apparent to those skilled in the art.

EXAMPLES

Example 1

Table 1 showed the inhibitory effect of chelerythrine on the thromboxane B2 formation of platelets induced by the arachidonic acid, collagen, ionophore A23187, or thrombin. In which, the platelets were preincubated with chelerythrine (10 ug/ml) or DMSO (0.5%) (control) at 37° C. for 3 minutes, followed by the addition of the aggregate inducer. The data were represented with average values ± S.E. (n).

TABLE 1

Inhibitory effect of chelerythrine on the thromboxane B2 formation of platelets

| Aggregate inducer | Thromboxane B2 (ng/ml) | |
|---|---|---|
| | Control | Chelerythrine |
| Arachidonic acid (100 uM) | 252.8 ± 35.6 (4) | 22.0 ± 2.4 (4)*** |
| Collagen (10 ug/ml) | 340.8 ± 29.7 (6) | 15.8 ± 2.4 (6)*** |
| Ionophore A23187 (5 uM) | 161.2 ± 40.2 (5) | 18.5 ± 4.2 (5)* |
| Thrombin (0.1 U/ml) | 219.9 ± 73.4 (4) | 9.4 ± 2.8 (4)** |

*$P < 0.05$;
**$P < 0.01$;
***$P < 0.01$ in comparison with the control.

Washed rabbit platelets were preincubated with chelerythrine (10 or 20 ug/ml) or DMSO (0.5%) (control) at 37° for 3 minutes, followed by the addition of the aggregate inducer such as ADP (20 uM), arachidonic acid (100 uM), PAF (2 ng/ml), collagen (10 ug/ml), ionophore A23187 (5 uM) or thrombin (0.1 U/ml). The data were represented by the average values ± S.E. (n=5-7), and the results were shown in the FIG. 1.

Figure 2:
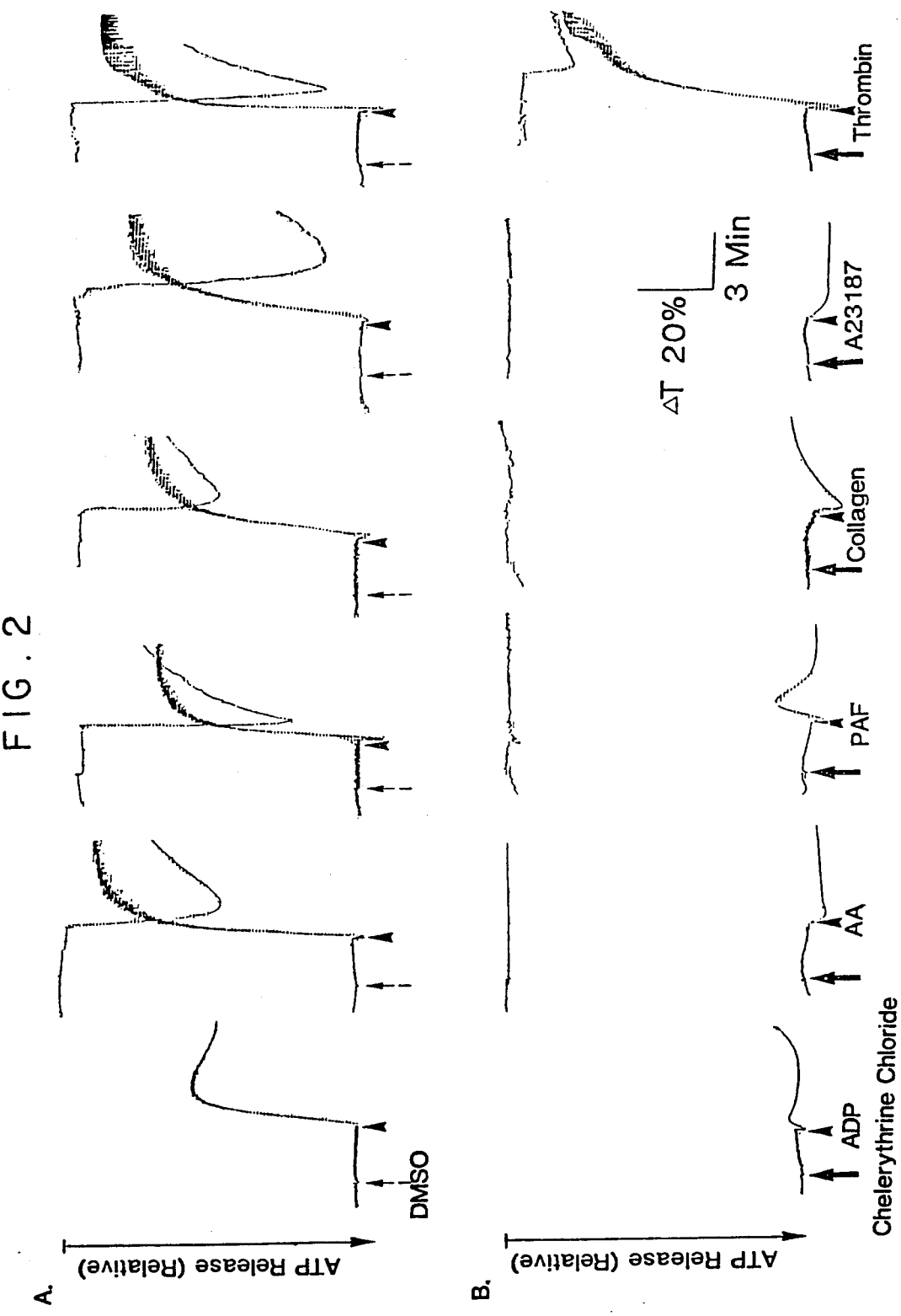
FIG. 2 shows the inhibitory effect of chelerythrine on the platelet aggregation and ATP release induced by ADP, arachidonic acid, PAF, collagen, ionophore A23187 and thrombin. Washed rabbit platelets were incubated with chelerythrine (10 μg/ml) or DMSO (0.5%) for 3 min, then ADP (20 μM), arachidonic acid (AA, 100 μM), PAF (2 ng/ml), collagen (10 μg/ml), ionophore A23187 (5 μM) or thrombin (0.1 U/ml) was added to trigger the aggregation (upward tracings) and ATP release (downward tracings).

As shown in FIG. 1, the chelerythrine completely inhibited the aggregation induced by the arachidonic acid, and PAF at concentration as low as 10 ug/ml. It also significantly inhibited the aggregation induced by the ADP and collagen. When chelerythrine was applied at 20 ug/ml, the aggregation induced by the thrombin can also be inhibited completely. In addition, the effects of chelerythrine found in this invention on the ATP release and the inhibition of platelet aggregation induced by ADP, arachidonic acid, PAF, collagen, ionophore A23187 and thrombin were shown in the FIG. 2. In this experiment, the washed platelets were preincubated with 10 ug/ml of chelerythrine or 0.5% DMSO for 3 minutes, followed by the addition of ADP (20 uM), arachidonic acid (AA, 100 uM), PAF (2 ng/ml), collagen (10 ug/ml), ionophore A23178 (5 uM) or thrombin (0.1 U/ml) to induce the platelet aggregation (upward arrow), and ATP release (downward arrow).

Figure 3:
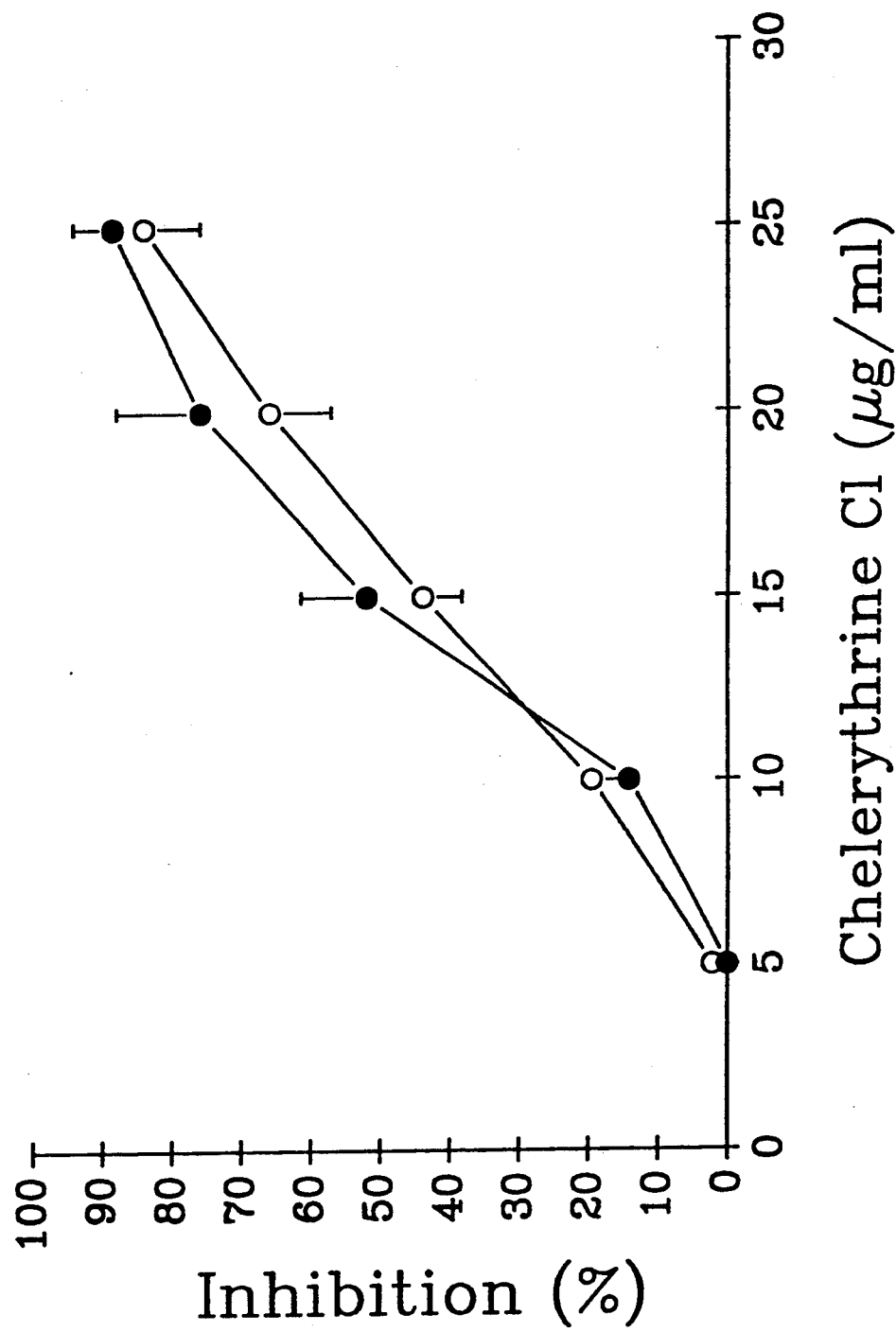
FIG. 3 shows concentration-dependent inhibition of chelerythrine on the fibrinogen-induced aggregation of elastase-treated rabbit (●- - -●) and human (○- - -○) platelets. Platelets were preincubated with chelerythrine of various concentrations or DMSO (0.5%, control) at 37° C. for 3 min, then fibrinogen (300 μg/ml) was added. Values are presented as % inhibition in means±S.E. (n=4).
Figure 4:
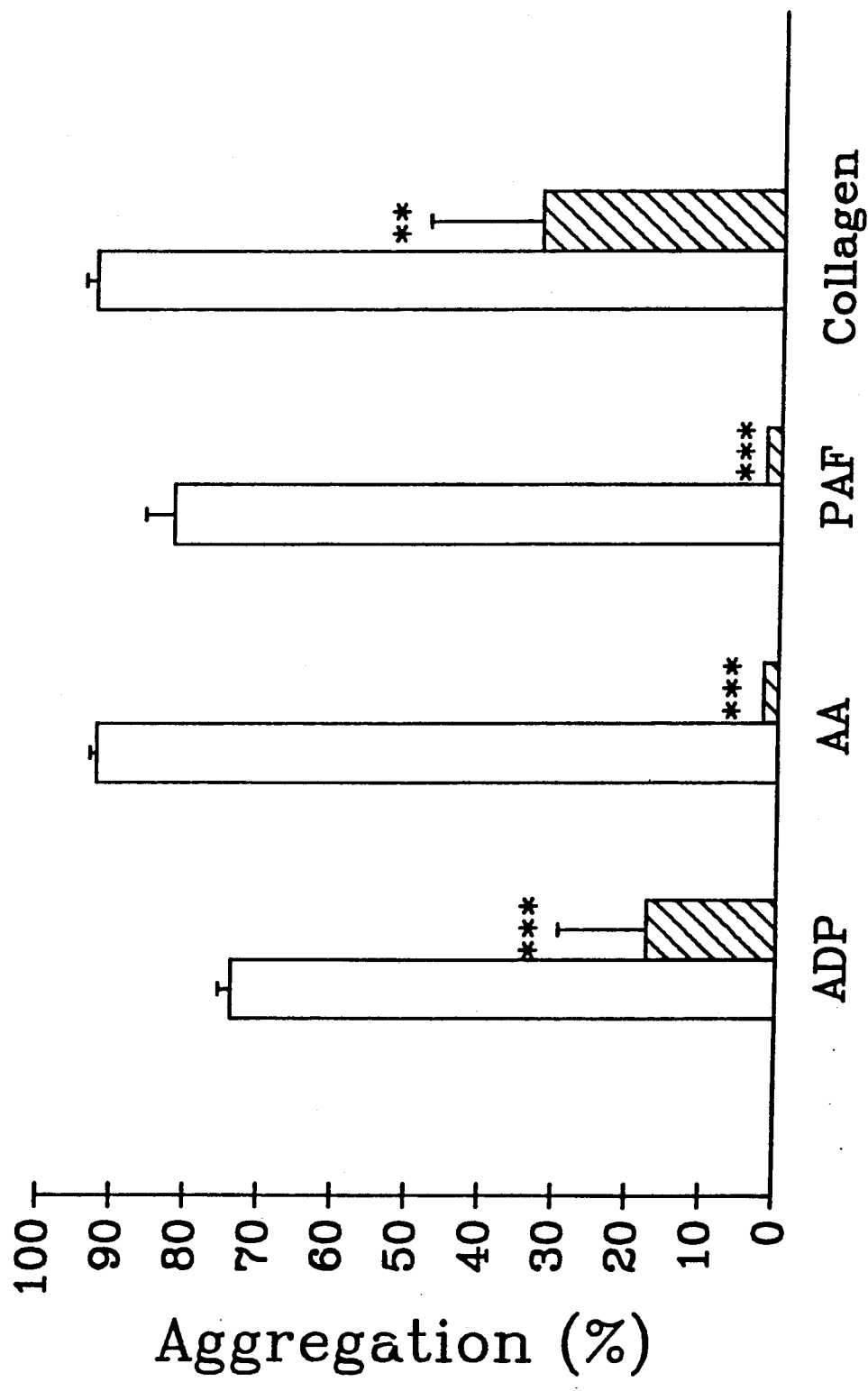
FIG. 4 shows the effect of chelerythrine on the aggregation of rabbit platelet-rich plasma induced by ADP (20 μM), arachidonic acid (AA, 100 μM), PAF (2 ng/ml) and collagen (10 μg/ml). Rabbit platelet-rich plasma was preincubated with chelerythrine (50 μg/ml) or DMSO (0.5%, control) at 37° C. for 3 min, then the inducer was added. Values are presented as means±S.E. (n=4). : $P<0.01$, *: $P<0.001$ as compared with the respective control.

The inhibitory effects of the chelerythrine chloride found in this invention on the platelet aggregation is concentration dependent. It inhibited the aggregation of rabbit platelet as strong as human platelet. The results were shown in FIG. 3. The $IC_{50}$ of chelerythrine chloride is 15 ug/ml, and the maximal inhibition is at 25 ug/ml. In the PRP, the inhibitory effect of chelerythrine is significantly decreased, it required 5× concentration (50 ug/ml) to completely inhibit the platelet aggregation induced by the arachidonic acid and PAF (see FIG. 4 for the reference).

What is claimed is:
1. A method for the treatment of patients with thromboembolism associated with abnormal activation of platelet aggregation comprising administering to said patient an effective amount of chelerythrine.
2. A method for the treatment of patients with peripheral ischemia associated with spasms of blood vessels comprising administering to said patient an effective amount of chelerythrine.

* * * * *